United States Patent [19]

Cook et al.

[11] Patent Number: 5,478,341
[45] Date of Patent: Dec. 26, 1995

[54] RATCHET LOCK FOR AN INTRAMEDULLARY NAIL LOCKING BOLT

[75] Inventors: Kevin S. Cook; S. Kyle Hayes, both of Warsaw; James R. Toone, Fort Wayne, all of Ind.

[73] Assignee: Zimmer, Inc., Warsaw, Ind.

[21] Appl. No.: 811,638

[22] Filed: Dec. 23, 1991

[51] Int. Cl.⁶ ............................ A61B 17/56; A61B 17/58
[52] U.S. Cl. ........................ 606/62; 606/96; 606/97
[58] Field of Search ............................. 606/59, 60, 61, 606/62, 66, 86, 87, 88, 96, 97

[56] References Cited

U.S. PATENT DOCUMENTS

| | | | |
|---|---|---|---|
| 4,135,505 | 1/1979 | Day | 606/59 |
| 4,488,542 | 12/1984 | Helland | 606/59 |
| 4,615,338 | 10/1986 | Ilizarov | 606/59 |
| 4,628,922 | 12/1986 | Dewar | 606/59 |
| 4,786,063 | 11/1988 | Engelhardt | 606/87 |
| 4,911,179 | 3/1990 | Brown | 128/875 |
| 4,913,137 | 4/1990 | Azer | 606/96 |
| 4,946,459 | 8/1990 | Bradshaw | 606/62 |
| 4,957,495 | 9/1990 | Kluger | 606/61 |
| 4,976,713 | 12/1990 | Landanger | 606/62 |
| 4,987,892 | 1/1991 | Krag | 606/61 |

Primary Examiner—Michael A. Brown
Attorney, Agent, or Firm—Todd A. Dawson

[57] ABSTRACT

This invention includes a ratchet wheel carried by the locking bolt and engaged by a pin carried by the targeting guide. The pin and ratchet wheel permit the locking bolt to rotate in a tightening direction and prevent the bolt from rotating in a direction to cause the bolt to loosen. Therefore, during impact, the bolt is prevented from loosening. After the IM rod is inserted and the surgeon wants to remove the targeting guide, the pin is shifted and locked into a disengaged position with the ratchet wheel to permit the locking bolt to rotate without obstruction. The ratchet pin may be locked in its retracted position.

6 Claims, 2 Drawing Sheets

RATCHET LOCK FOR AN INTRAMEDULLARY NAIL LOCKING BOLT

FIELD OF THE INVENTION

This invention relates to intramedullary rod drill alignment guides or targeting guides and has specific relevance to a ratchet lock for the locking bolt on drill alignment guides used with intramedullary nails.

BACKGROUND OF THE INVENTION

During a procedure to insert an intramedullary (IM) rod or nail, a proximal targeting guide is connected to the IM rod with a locking bolt. As is well known, the targeting guide provides alignment for drilling transverse bores through the bone to accommodate transverse screws to lock the rod to the bone. The locking bolt is threaded into the proximal end of the IM rod aligned generally with the longitudinal axis of the IM rod. During insertion, a mallet is used to strike a driver which communicates the impact through the proximal targeting guide to the IM rod. During normal use the locking bolt may loosen from repeated impacts from the driver. A loosened locking bolt may allow the targeting guide to shift slightly thereby compromising the integrity of the IM rod/targeting guide alignment.

SUMMARY OF THE INVENTION

This invention includes a ratchet wheel carried by the locking bolt and engaged by a pin carried by the targeting guide. The pin and ratchet wheel permit the locking bolt to rotate in a tightening direction and prevent the bolt from rotating in a direction to cause the bolt to loosen. Therefore, during impact, the bolt is prevented from loosening. After the IM rod is inserted and the surgeon wants to remove the targeting guide, the pin is shifted into a disengaged position with the ratchet wheel to permit the locking bolt to rotate without obstruction. The pin may be locked in the disengaged position in one embodiment of the application.

Accordingly, it is an object to provide for a novel targeting guide for an IM rod.

Another object of the invention is to provide for a targeting device for an IM rod having a anti-reverse mechanism associated with the locking bolt to prevent the locking bolt from loosening during impact.

Another object of the invention is to provide for a ratchet lock for a locking bolt on an IM rod targeting device.

Still other objects of the invention will become apparent upon a reading of the following description taken with the accompanying drawings.

DESCRIPTION OF THE PREFERRED EMBODIMENTS

Figure 1:
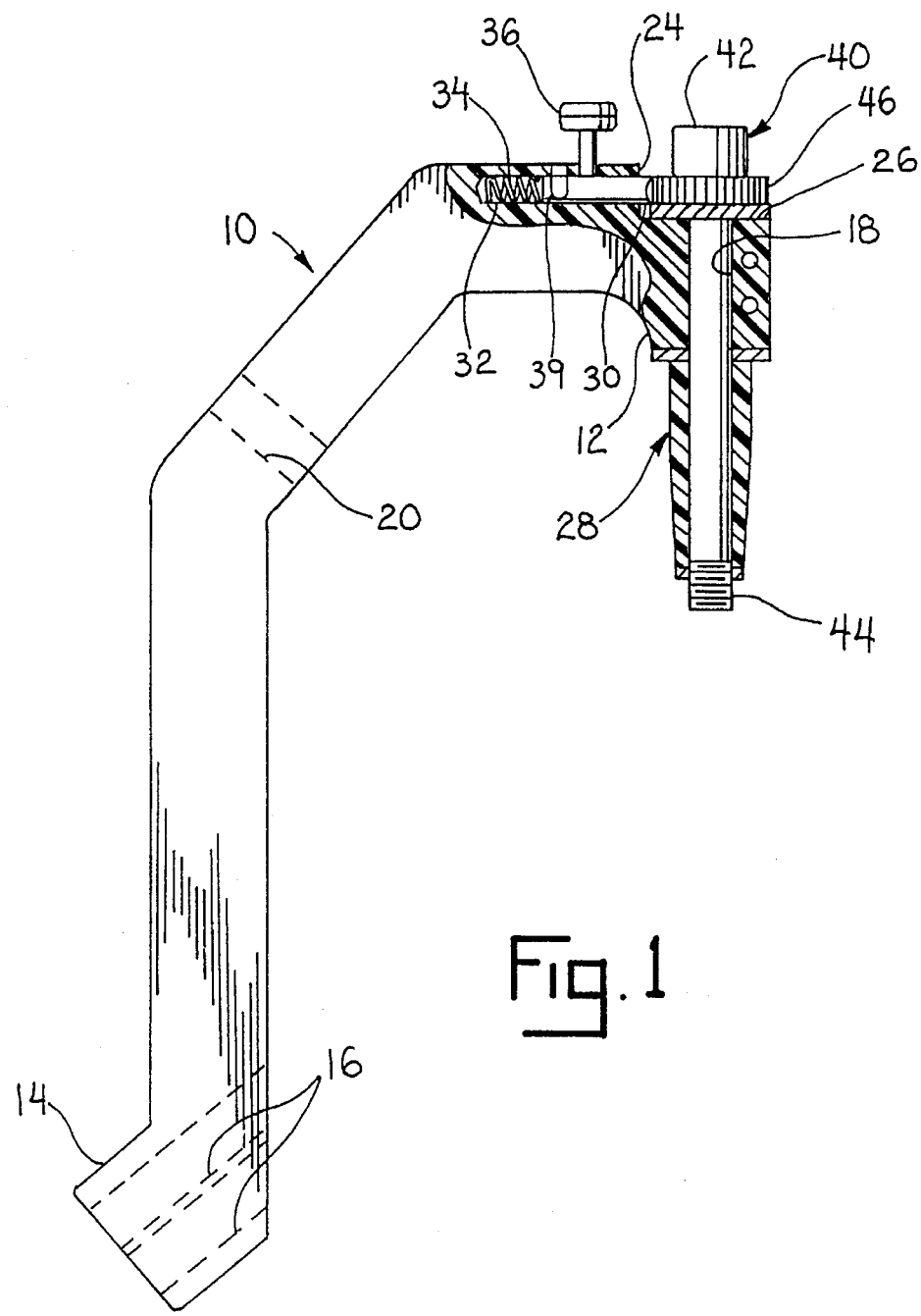
FIG. 1 is a side elevational view of the targeting device having a ratchet lock for the locking bolt.

The preferred embodiments herein described are not intended to be exhaustive or to limit the invention to the precise forms disclosed. Rather, they are chosen and described to best explain the invention so that others skilled in the art might utilize their teachings.

Referring now to the drawings, a proximal targeting guide 10 is illustrated as including a rod engaging end 12 and a drill alignment end 14. As illustrated, guide 10 is generally an inverted L shape. A pair of drill guide bores 16 are formed through end 14 of guide 10. A throughbore 18 is formed in end 12. A drill guide bore 20 is formed through guide 10 at a position between end 12 and end 14. A recess is formed in end 12 forming shoulders 24 and 26. A barrel insert 28 is inserted into bore 18 and extends away from end 12 as illustrated in the figures. Insert 28 includes protrusions for mating with the proximal end of the IM rod (not shown). A bolt action ratchet pin 30 is carried within a blind bore 32 of guide 10 and extends outwardly from shoulder 24. A helical spring 34 is carried within bore 32 to bias pin 30 toward shoulder 24. A handle 36 is connected to pin 30 and extends generally transversely relative to the pin. An L-shaped slot 38 is formed in guide 10 in communication with blind bore 32. Pin 30 is shiftable between the extended position illustrated in the figures and a retracted locked position wherein handle 36 seats within the transverse section 39 of slot 38. In the retracted position, pin 30 is completely housed within bore 32.

A locking bolt 40 having a head 42 and a threaded shaft 44 is carried by guide 10 such that shaft 44 extends through the center bore of guide barrel 28. Locking bolt 40 is provided to connect the guide 10 to the IM rod, not shown, by the accommodation of the distal tip of shaft 44 in a central threaded bore of the IM rod. A ratchet wheel 46 having a plurality of ratchet teeth is carried on the shaft 44 of the locking bolt 40 adjacent head 42. Ratchet wheel 46 is rotationally fixed to locking bolt 40. Ratchet wheel 46 is supported on shoulder 26 so as to be in lateral alignment with ratchet pin 30.

Figure 2:
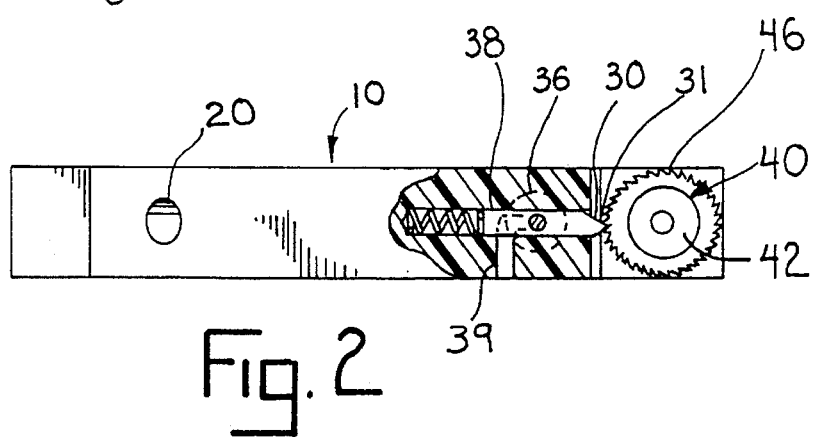
FIG. 2 is an elevational view taken from the top down of the targeting guide of FIG. 1.

In use, barrel 28 is placed in contact with the IM rod in a common manner and locking bolt 40 is rotated to threadibly connect the locking bolt and guide to the IM rod. Initially, ratchet pin 30 is in its retracted and locked position with handle 36 seated within section 39 of the L-shaped slot. Once the locking bolt is tightened appropriately, handle 36 is pulled from section 39 by the surgeon. Spring 34 then urges pin 30 toward the ratchet wheel such that the beveled distal tip 31 of the ratchet pin seats within a notch formed between an adjacent pair of ratchet wheel teeth. The angled orientation of the ratchet teeth and the tip 31 of pin 30 prevents the locking bolt from rotating clockwise in FIG. 2 to thereby prevent the bolt from loosening during insertion of the rod. However, the engagement between the ratchet teeth and locking pin permits the locking bolt to rotate in a direction to tighten the locking bolt. When the surgeon wants to remove guide 10 from the rod, handle 36 is pulled rearwardly to disengage pin 30 from wheel 40. Handle 36 is again seated within section 39 of slot 32 to lock the pin in the retracted position. The surgeon may now connect a Hex Head driver (not shown) or similar removal tool to head 42 to turn shaft 44 from the IM rod.

It should be understood that the exact configuration of guide 10 and the location of the drill guide bores is substantially dependant upon the IM rod to be inserted. The figures identifying the shape of the guide and location of the guide holes are shown for illustrative purposes only.

Figure 3:
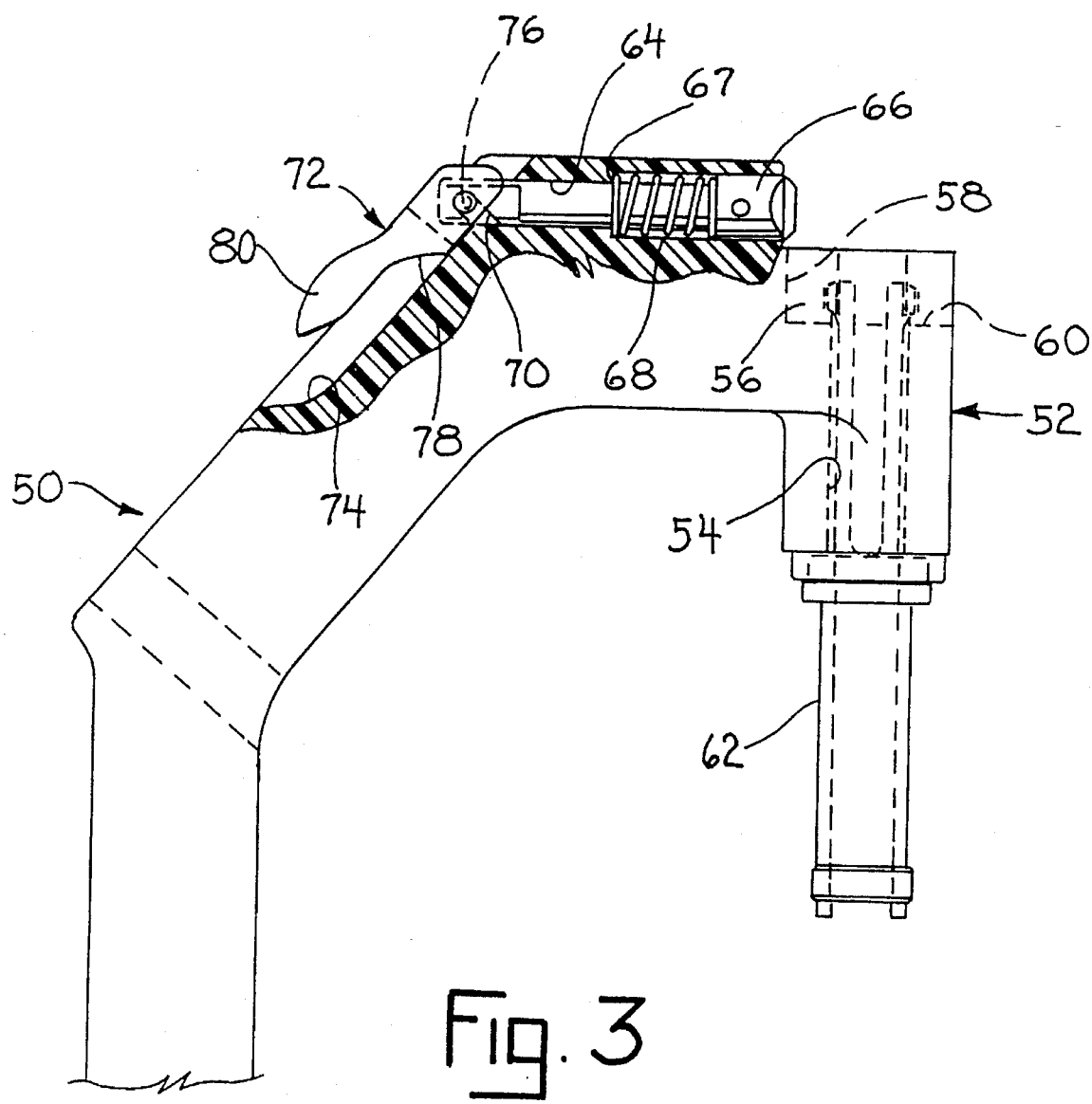
FIG. 3 is a partial side elevational view of an alternative embodiment with portions sectioned for illustrative purposes only.

Referring now to FIG. 3, an alternative embodiment of the locking pin is illustrated. Targeting guide 50 includes a drill alignment end (not shown) and a rod engaging end 52. A throughbore 54 is formed in end 52. A recess 56 is formed in end 54 forming shoulders 58 and 60. A barrel insert 62 is inserted into bore 54 and extends away from end 52 as illustrated. A throughbore 64 is formed in end 52 and is generally transverse to throughbore 54. Throughbore 64 includes an internal shoulder 67. A ratchet pin 66 is carried within bore 64 and is biased outwardly from shoulder 58 by a helical spring 68. One end of pin 66 includes a angled groove 70. A cam lever 72 is seated within a recess 74 of guide 50 includes a transverse pin 76 which is seated within the angled groove 70 of ratchet pin 66. Lever 72 includes a fulcrum portion 78 and a handle portion 80. Spring 68 biases pin 66 toward shoulder 58 which causes cam lever 72 to abut guide 50 at fulcrum 78 such that handle 80 is spaced from the guide. The targeting guide may then be used in a manner consistent with the use of guide 10 of FIGS. 1 and 2. The handle portion 80 of cam lever 72 is pushed toward guide 50 which pivots the cam lever about its fulcrum 78 and draws pin 66 into bore 64 and clear of recess 56 so that the locking bolt (not shown) may be removed. On release of the handle, spring 68 biases the ratchet pin into its retracted position into its extended position.

It should be further understood that the invention is not to be limited to the precise form disclosed but may be modified within the scope of the appended claims.

We claim:

1. A locking system for a locking bolt of a proximal targeting guide for an intramedullary rod and a locking bolt, said locking system comprising a ratchet wheel carried by said locking bolt and rotational fixed thereto, said ratchet wheel including a plurality of teeth about a perimeter of said wheel, a locking pin carried by said guide for engagement with said wheel and shiftable between an extended position wherein said pin engages said wheel and seats within a groove formed between adjacent pairs of teeth and a retracted position wherein said pin is disengaged from said wheel, wherein with said pin in said extended position said locking bolt is permitted to rotate in only one direction.

2. The locking system of claim 1 and including means for locking said pin in said retracted position.

3. A proximal targeting guide for an intramedullary rod, said targeting guide comprising a body having a plurality of bores therethrough, a portion of said bores constituting drill alignment guides, a bolt extending through one of said openings, said bolt adapted for threadible accommodation within said intramedullary rod to lock said targeting guide to said rod, ratchet means carried by said targeting guide for permitting rotation of said bolt in only one direction.

4. The proximal targeting guide of claim 3 wherein said ratchet means includes a wheel carried by said bolt, said wheel including a plurality of ratchet teeth formed about the periphery of said wheel, a ratchet pin being carried by said targeting guide for engaging with said wheel, said pin being shiftable between an extended position wherein said pin engages said wheel and a retracted position wherein said pin is disengaged with said wheel, wherein with said pin in said extended position and said pin engaged with said wheel between an adjacent pair of said teeth, said wheel and said bolt are permitted to rotate in only one direction relative to said pin.

5. The proximal targeting guide of claim 4 wherein said pin includes a handle extending generally transversely from said pin, a slot being formed in said targeting guide for accommodating said handle, said slot including a transverse portion, wherein with said handle positioned within said transverse portion, said pin is locked in said retracted position.

6. The proximal targeting guide of claim 4 and including spring means for biasing said pin toward its extended position.

* * * * *